United States Patent [19]

Zehner et al.

[11] Patent Number: 4,778,929
[45] Date of Patent: Oct. 18, 1988

[54] CONTINUOUS HYDROFORMYLATION OF OLEFINICALLY UNSATURATED COMPOUNDS

[75] Inventors: Peter Zehner, Ludwigshafen; Herwig Hoffmann, Frankenthal; Wolfgang Richter, Wachenheim; Dieter Stuetzer, Dudenhofen; Max Strohmeyer, Limburgerhof; Helmut Walz, Ludwigshafen; Erich Weippert, Mannheim, all of Fed. Rep. of Germany

[73] Assignee: BASF Aktiengesellschaft, Ludwigshafen, Fed. Rep. of Germany

[21] Appl. No.: 70,963

[22] Filed: Jul. 8, 1987

[30] Foreign Application Priority Data

Jul. 25, 1986 [DE] Fed. Rep. of Germany ....... 3625261

[51] Int. Cl.$^4$ .............................................. C07C 45/50
[52] U.S. Cl. ...................................... 568/454; 568/451
[58] Field of Search .......................... 568/451, 453, 454

[56] References Cited

U.S. PATENT DOCUMENTS

| | | | |
|---|---|---|---|
| 3,271,458 | 9/1966 | Ellis et al. | 568/453 |
| 3,518,319 | 6/1970 | Ellert et al. | 568/453 |
| 3,527,809 | 9/1970 | Pruett et al. | 568/454 |
| 4,247,486 | 1/1981 | Brewster et al. | 568/454 |
| 4,523,036 | 1/1985 | Cornila | 568/454 |
| 4,577,043 | 3/1986 | Kalbfell et al. | 568/454 |

FOREIGN PATENT DOCUMENTS

| | | | |
|---|---|---|---|
| 157755 | 10/1985 | European Pat. Off. | 568/454 |
| 1186455 | 2/1965 | Fed. Rep. of Germany | 568/454 |
| 3114147 | 10/1982 | Fed. Rep. of Germany | 568/454 |
| 3301591 | 7/1984 | Fed. Rep. of Germany | 568/454 |

Primary Examiner—Werren B. Lone
Attorney, Agent, or Firm—John H. Shurtleff

[57] ABSTRACT

Olefinically unsaturated compounds are hydroformylated continuously, the olefin being passed into the lower region of the reactor, under from 1 to 40 bar and at from 50° to 140° C. with the aid of a rhodium complex as a catalyst in a hydroformylation reactor having a liquid reaction zone which occupies about 60–85% of the reactor volume, the gaseous products and reactants being removed from the hydroformylation reactor, the products being isolated and the major part of the remaining gas being recycled to the reactor by the cycle gas method, by a process in which from 20 to 80% by volume of the cycle gas is fed into the hydroformylation reactor above the liquid reaction zone and/or below the liquid surface in the top fourth of the liquid reaction zone.

16 Claims, 1 Drawing Sheet

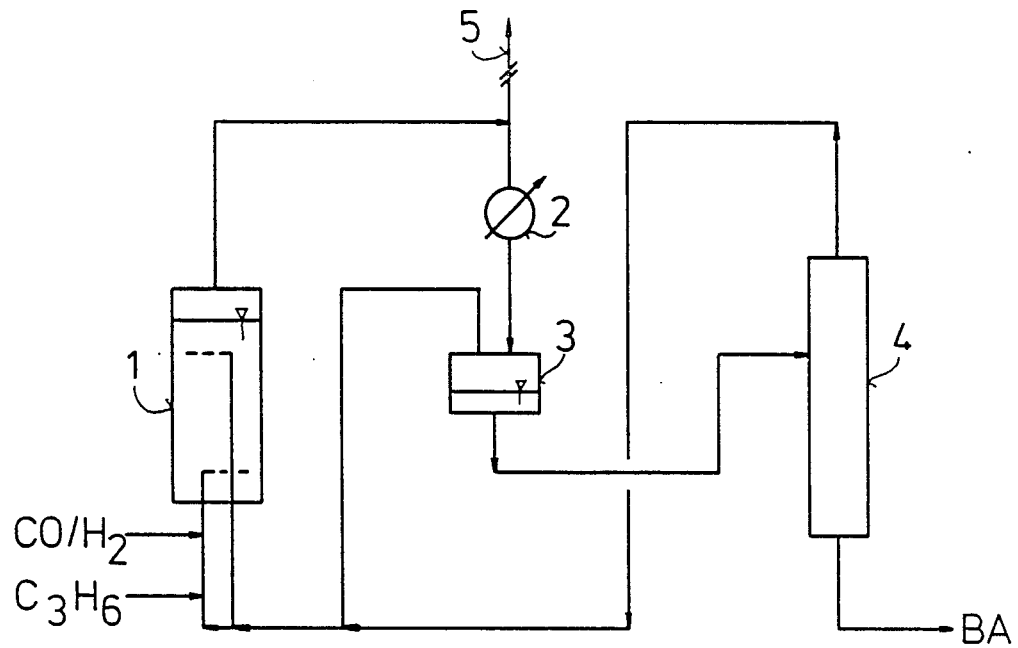

CONTINUOUS HYDROFORMYLATION OF OLEFINICALLY UNSATURATED COMPOUNDS

The present invention relates to an improved process for the continuous hydroformylation of olefinically unsaturated compounds, the olefin being passed into the lower region of the reactor, under from 1 to 40 bar and at from 50° to 140° C. with the aid of a rhodium complex as a catalyst in a hydroformylation reactor having a liquid reaction zone which occupies about 60–85% of the reactor volume, the gaseous products and reactants being removed from the hydroformylation reactor, the products being isolated and the major part of the remaining gas being recycled to the reactor by the cycle gas method.

The hydroformylation of olefinically unsaturated compounds by means of rhodium catalysts is generally known, for example from Chemical Engineering, December 1977, pages 110–115, or German Laid-Open Applications DOS 3,301,591, DOS 1,793,069 and DOS 1,186,455. Furthermore, the use of the cycle gas method, in which the products, ie. predominantly aldehydes and also the corresponding alcohols, are discharged from the reactor in vapor form together with gaseous reactants, the products are isolated from the gas stream, and the major part of the remaining gases, which essentially contain carbon monoxide, hydrogen and unconverted olefin, is recycled to the liquid zone of the reactor, has been disclosed in, for example, DE-A No. 27 15 685 and DE-A No. 31 14 147.

Although this process gives good results, it is an object of the present invention further to improve the yield of the products, ie. the aldehydes.

We have found that this object is achieved by a process for the continuous hydroformylation of olefinically unsaturated compounds, the olefin being passed into the lower region of the reactor, under from 1 to 40 bar and at from 50° to 140° C. with the aid of a rhodium complex as a catalyst in a hydroformylation reactor having a liquid reaction zone which occupies about 60–85% of the reactor volume, the gaseous products and reactants being removed from the hydroformylation reactor, the products being isolated and the major part of the remaining gas being recycled to the reactor by the cycle gas method, wherein from 20 to 80% by volume of the cycle gas is fed to the hydroformylation reactor above the liquid reaction zone and/or under the liquid surface in the top fourth of the liquid reaction zone.

In the novel process, the cycle gas is not fed in at the bottom of the reactor, into the liquid zone which occupies about ⅔ of the reactor volume, as has been usual hitherto; instead, from 20 to 80% by volume of the cycle gas is introduced directly into the vapor space above the hydroformylation mixture consisting of liquid and gaseous components and/or below the liquid surface in the top fourth of the liquid reaction zone, addition below the liquid surface being particularly preferred. Good increases in yield can be achieved in particular when from 40 to 60% by volume of the cycle gas is introduced in the manner according to the invention. The remaining cycle gas can be fed in either at the bottom of the reactor or, advantageously, in part streams at different heights. It is surprising that the measure according to the invention results in an increase in yield, since it was to be expected that recycling of all the cycle gas together with the fresh gas to the bottom of the reactor would promote aldehyde formation owing to the fairly large amount of starting materials supplied.

The effect of the novel procedure is particularly evident when reactions are carried out on a large industrial scale. It is generally true that the effect increases with the dimensions of the reactor. Reactor types having a diameter of 1 m or more and a height of not less than 5 m are therefore particularly preferred. Advantageously, the diameter is from 1 to 5 m, in particular from 2 to 4 m, and the height from 5 to 30 m, in particular from 15 to 30 m.

The novel procedure makes it possible to achieve further increases in conversion by the use of larger amounts of rhodium. Whereas to date it has been impossible to increase the conversion significantly by increasing the rhodium concentration, which is usually from 100 to 150 ppm, based on the liquid reaction mixture, it has now been found that a larger amount of rhodium affects the conversion, the latter increasing proportionally to the amount of rhodium. Rhodium concentrations of about 120–500 ppm, in particular 150–500 ppm, based on the liquid reaction mixture, are therefore preferably chosen.

In another embodiment of the process, the $CO/H_2$ gas volume required for the hydroformylation can be divided up and the part streams fed into the liquid reaction zone at different heights. For example, about 80–20, in particular 40–20, % by volume of the $CO/H_2$ gas can be fed in at the bottom of the reactor and the remainder at one or more levels, advantageously from 3 to 5 levels of different heigths above the bottom fifth of the liquid reaction zone. For example, it is possible for about 40–20% by volume of the $CO/H_2$ mixture to be passed in at the bottom of the reactor and the remainder into the second, third and fourth fourths of the liquid reaction zone.

When all the gas is introduced at the bottom of the reactor according to the prior art, a CO gradient of about 10% forms up to the surface of the hydroformylation mixture; this gradient can be reduced to about 2% by the metering procedure described.

By feeding the cycle gas into the reactor in accordance with the invention and, if necessary, dividing up the $CO/H_2$ mixture, it is intended to prevent the accumulation of large amounts of cycle gas or fresh gas. It is therefore superfluous to describe further possible methods of introducing the part streams of gas, since the present description makes it possible for the skilled worker to divide up the gas volume in a useful manner.

Apart from the improvement according to the invention, the process can be carried out in a conventional manner, both in the hydroformylation stage and for the isolation of the products from the gas stream, so that detailed descriptions of these procedures can be dispensed with. Hence, only a few fundamental explanations are given below.

Hydroformylation of the olefins is carried out under from 1 to 40 bar and at from 50° to 140° C. Suitable olefins are in general α-olefins which may contain functional groups which are inert under the reaction conditions, eg. allyl alcohol, allyl acetate, lower molecular weight acrylates and acrolein acetals.

Lower olefins of 2 to 4 carbon atoms, eg. ethylene, propylene and but-1-ene, are preferably reacted since the aldehydes formed have a high partial pressure, making discharge in vapor form worthwhile.

Suitable catalysts for the hydroformylation are rhodium complexes which contain, as ligands, sparingly volatile compounds I

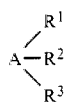

where A is phosphorus, arsenic, antimony or bismuth and $R^1$, $R^2$ and $R^3$ are each organic radicals.

As a rule, the compounds I are used in a 3-fold to 500-fold molar excess, based on the rhodium, and the rhodium complex is formed in situ in the hydroformylation mixture from rhodium salts, eg. the acetate. Of course, it is also possible to add the separately prepared, complete rhodium complex.

The choice of the ligands I may depend on the specific aims in individual cases. In general, triorganophosphorus compounds, such as triaryl- or aryl-alkylphosphines and trialkyl, triaryl or arylalkyl phosphites, are used. Trialkylphosphines are generally not so suitable. Particularly preferred organophosphorus compounds are triarylphosphines, such as triphenyl- or tritolylphosphine, or aryl-alkylphosphines, such as diphenyl-$C_1$-$C_8$-alkylphosphines.

Depending on the hydroformylation task, the CO/$H_2$ molar ratio can be from about 10:90 to 90:10. It is advantageously from 45:55 to 55:45 if the desired products are aldehydes, which is generally the case.

The products can be isolated from the gaseous reacted mixture in a conventional manner, for example as described in Chemical Engineering, 1977, page 110 et seq. or German Laid Open Application DOS No. 3,114,147. For example, the gas mixture can be cooled in a cooler until the products have substantially become liquid and can be isolated by means of a separator. This liquid phase can then be passed through a degassing column in order to recover dissolved olefins, before being worked up by distillation. The gases obtained from the separator and the degassing column and essentially containing unconverted olefin, the corresponding paraffin and CO and $H_2$ are, for the major part, compressed and recycled to the reactor as cycle gas. To prevent the amount of useless gases, such as paraffin and nitrogen, from increasing continuously, some of the cycle gas must be removed from the system as waste gas. For lower olefins, eg. ethylene, it is advantageous to select the procedure described in German Laid Open Application DOS No. 3,114,147, in which the gaseous reacted mixture is fed to a distillation column without being cooled or let down, the top fraction from this column is cooled in a cooler until the predominant parts of the aldehydes present therein have condensed, and the condensate is separated into a gas phase and a liquid phase in a separator. The liquid phase is recycled to the distillation column and the aldehyde is removed as a liquid bottom product and/or as a vapor side stream. The gas phase is recycled to the hydroformylation reactor, as described above, after removal of the waste gas, which accounts for about 1–5% by volume of the cycle gas, and compensation of the pressure loss by means of a compressor; this recycling is effected in such a way that not less than 20% by volume enters above the liquid surface or is introduced into the top fourth of of the liquid reaction zone of the reactor.

Compared with the conventional procedure, the novel process makes it possible to increase the aldehyde yield by not less than about 5–10%, the n/iso ratio observed to date remaining unchanged.

EXAMPLE 1

Hydroformylation of propylene

1(a) 488 kg/hour of propylene, 228.4 $m^3$ (S.T.P.)/hour of CO and 270 $m^3$ (S.T.P.)/hour of $H_2$ were introduced into an experimental reactor which was about ⅔ full of butyraldehyde condensates, and were subjected to hydroformylation in a conventional manner in the presence of 153 ppm of rhodium and 3.8% by weight of triphenylphosphine, the amounts being based on the reaction mixture (ratio of rhodium to triphenylphosphine=about 98:1), at 110° C. and under 16 bar. The products were removed from the reactor in gaseous form, together with unconverted starting materials, and were separated in a conventional manner. 40% by volume of the cycle gas was recycled to the reactor about 15% below the surface of the liquid reaction zone.

1(b) This experiment was repeated under the same conditions, except that the cycle gas was fed in at the bottom of the reactor, into the liquid hydroformylation mixture, a smaller amount of CO and $H_2$ being consumed.

Results of the two experiments are summarized in the Table below.

|  | Experiment | |
|---|---|---|
|  | 1a according to the invention | 1b comparison |
| Propylene conversion, % Including | 92 | 85.7 |
| n-butyraldehyde, % | 75.3 | 69.9 |
| isobutyraldehyde, % | 12.2 | 11.4 |
| Propane, % | 2.0 | 2.0 |
| Ratio of n-aldehyde to iso-aldehyde | 86:14 | 86:14 |

EXAMPLES 2 AND 3

In a reactor having a length of 22 m and a diameter of 2.80 m, propylene was reacted with oxo gas to give butyraldehydes. The experimental setup is shown schematically in the FIGURE. The starting materials propylene and oxo gas, together with some of the cycle gas or with all of the cycle gas (Comparative Examples 2b and 3b), were introduced at the bottom of the reactor (1), via a distribution apparatus, into the liquid phase predominantly consisting of butyraldehyde condensates and occupy-about ⅔ of the reactor volume. A second cycle gas stream was fed in below the liquid surface in the top fourth of the liquid reaction zone, via a similar distribution apparatus.

The product was discharged in proportion to its vapor pressure, via the cycle gas, and was condensed out in a cooler (2) and collected (3). The $C_3$ fractions (propylene and propane) also condensed were removed in gaseous form in a separate column (4) and recycled in the circulation. The propane was separated off via a separate waste gas stream (5).

Table 2 below shows the resulting propylene conversions as a function of the reaction conditions, such as the method of metering the oxo gas and the rhodium concentration. All reactions were carried out at 100° C. under partial pressures $P(C_3H_6)=4.8$ bar, $P(H_2)=8.0$ bar and P(CO)=0.6 bar. The ratio of rhodium to triphenylphosphine was 1:120 in each case.

TABLE 2

| | | | Hydroformylation of propylene | | | |
|---|---|---|---|---|---|---|
| Example | Cycle gas kg/h | Metering* | Rh concentration ppm | Propylene consumption kg/h | Butyraldehyde formation kg/h | n/iso | Propylene conversion % |
| 2a | 9270 | bottom | 160 | 3997 | 5687 | 84/16 | 83.8 |
|    | 13300 | top | | | | | |
| 2b | 17700 | bottom | 163 | 3280 | 4680 | 85/15 | 83.2 |
| 3a | 9390 | bottom | 188 | 4399 | 6504 | 86/14 | 86.3 |
|    | 16870 | top | | | | | |
| 3b | 18100 | bottom | 190 | 3200 | 4600 | 85/15 | 83.8 |

*Bottom = at the bottom of the reactor
Top = below the liquid surface, in the top fourth of the liquid reaction zone

We claim:
1. In a process for the continuous hydroformylation of an olefin of 2 to 4 carbon atoms with a $CO/H_2$ gas mixture to form an aldehyde product, a fresh olefin feed being passed into the lower region of a reactor, under from 1 to 40 bar and at from 50° to 140° C. and being hydroformylated with the aid of a rhodium complex as a catalyst in a liquid reaction zone which occupies about 60-85% of the reactor volume, the gaseous products and reactants being removed from said reactor, the products being isolated and the major part of the remaining gas being recycled to the reactor by the cycle gas method, the improvement which comprises:
feeding from 20 to 80% by volume of the cycle gas to the hydroformylation reactor above the liquid reaction zone or under the liquid surface in the top fourth of the liquid reaction zone.

2. A process as claimed in claim 1, wherein from 40 to 60% of the cycle gas is fed in below the liquid surface in the top fourth of the liquid reaction zone.

3. A process as claimed in claim 1, wherein the rhodium concentration is from 120 to 500 ppm, based on the liquid reaction mixture.

4. A process as claimed in claim 1, wherein the $CO/H_2$ mixture required for the hydroformylation is divided up and the part streams are fed into the liquid reaction zone at different heights.

5. A process as claimed in claim 1, wherein about 80-20% by volume of the $CO/H_2$ mixture is fed in at the bottom of the reactor and the remainder at one or more levels above the bottom fifth of the liquid reaction zone.

6. A process as claimed in claim 1, which is applied to the hydroformylation of an α-olefinically unsaturated compound.

7. A process as claimed in claim 1, wherein a $C_1$-$C_4$-olefin is converted.

8. A process as claimed in claim 1, wherein the rhodium complex contains, as a ligand, a sparingly volatile compound of the formula I

where A is phosphorus, arsenic, antimony or bismuth and $R^1$, $R^2$ and $R^3$ are each organic radicals.

9. A process as claimed in claim 1, wherein the rhodium complex contains a triaryl- or aryl-alkylphosphine as a ligand.

10. A process as claimed in claim 1, wherein the continuous hydroformylation is carried out in a reactor having a diameter of at least 1 meter and a height of not less than 5 meters.

11. A process as claimed in claim 10, wherein the reactor diameter is from 1 to 5 meters and its height is from 5 to 30 meters.

12. A process as claimed in claim 11, wherein the rhodium concentration is about 120-500 ppm.

13. A process as claimed in claim 11, wherein the rhodium concentration is about 150-500 ppm.

14. A process as claimed in claim 1, wherein the olefin is propylene.

15. A process as claimed in claim 1, wherein the total $CO/H_2$ gas mixture introduced into the reactor has a molar ratio of $CO:H_2$ maintained at about 45:55 to 55:45.

16. A process as claimed in claim 15, wherein about 20 to 40% of the $CO/H_2$ gas mixture is fed in at the bottom of the reactor, the remainder being fed at from 3 to 5 levels above the bottom fifth of the liquid reaction zone, provided that at least 20% by volume of the cycle gas is fed into the top fourth of the liquid reaction zone.

* * * * *